United States Patent [19]

Vorbrüggen et al.

[11] 4,109,078
[45] Aug. 22, 1978

[54] N-(POLYSACCHARIDYL)-NITROGEN HETEROCYCLES, ESPECIALLY PYRIMIDINE OR PURINE BASES, AND PROCESS FOR THEIR PREPARATION

[75] Inventors: Helmut Vorbrüggen; Ulrich Niedballa, both of Berlin, Germany

[73] Assignee: Schering Aktiengesellschaft, Berlin and Bergkamen, Germany

[21] Appl. No.: 670,741

[22] Filed: Mar. 26, 1976

[30] Foreign Application Priority Data

Mar. 27, 1975 [DE] Fed. Rep. of Germany ....... 2514275

[51] Int. Cl.$^2$ .................... C07H 19/06; C07H 19/16
[52] U.S. Cl. ........................ 536/26; 536/22; 536/23; 536/24; 536/31; 536/46
[58] Field of Search ............... 536/22, 23, 24, 26, 536/31, 46

[56] References Cited

U.S. PATENT DOCUMENTS

| | | | |
|---|---|---|---|
| 2,828,302 | 3/1958 | Mitz | 536/24 |
| 2,949,450 | 8/1960 | Stark | 536/23 |
| 3,352,849 | 11/1967 | Shen et al. | 536/23 |
| 3,354,160 | 11/1967 | Duschinsky et al. | 536/23 |
| 3,730,844 | 5/1973 | Gilham et al. | 536/24 |
| 3,748,320 | 7/1973 | Vorbruggen et al. | 536/23 |
| 3,891,623 | 6/1975 | Vorbruggen et al. | 536/23 |

Primary Examiner—Johnnie R. Brown
Attorney, Agent, or Firm—Millen & White

[57] ABSTRACT

Nucleosides of the formula

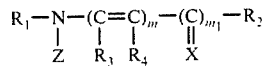

wherein
Z is a free or blocked polysaccharide residue;
X is O or S;
m is 0 or 1;
$m_1$ is 0 or 1;
$R_1$ and $R_2$ collectively are a saturated or unsaturated, optionally substituted bivalent organic radical containing up to two nitrogen atoms; and
$R_3$ and $R_4$ independently are hydrogen, alkyl, alkoxycarbonyl, alkylaminocarbonyl, carboxyl, or nitrile group, or collectively are one of the bivalent radicals

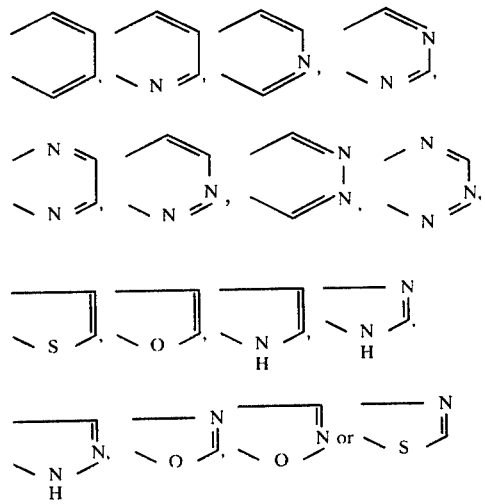

and substituted or hydrogenated analogs thereof, are sorbents useful for the separation of nucleoside mixtures.

15 Claims, No Drawings

N-(POLYSACCHARIDYL)-NITROGEN HETEROCYCLES, ESPECIALLY PYRIMIDINE OR PURINE BASES, AND PROCESS FOR THEIR PREPARATION

BACKGROUND OF THE INVENTION

Processes such as gel filtration, ion exchange chromatography, and affinity chromatography are known for the separation of complex mixtures of nucleic acids, enzymes, or other biopolymers. Whereas only crude classification, that is, separation according to molecule size or molecule charge, respectively, is possible with the first two methods, a component can be selectively separated or isolated by affinity chromatography.

Requirements of this method are that the component have specific properties and that the sorbent contain a ligand specific to this component. This ligand is to be linked, if possible, with the sorbent in a covalent fashion, since bleeding out can occur if the linkage is ionic or adsorptive. The method of base pairing is as a specific selection or principle for the separation of nucleic acids. The production of sorbents for the separation of nucleic acids, which are based on the principle of base pairing, is described in the literature. J. Chromatogr. 82, 349 (1973); Nucleic Acids Res. 1, 1587 (1974).

Known carrier materials are, for example, polysaccharides or polyamides and suitable ligands are purine nucleotides, pyrimidine nucleotides and polynucleotides linked to the carrier covalently.

The aforesaid methods require several stages. First, carrier material is activated to be able to bond with the ligand. Thereafter, unreacted active centers are deactivated.

Expensive and time-consuming washing procedures are required between the individual stages. Therefore, a method is needed which links carrier to ligand covalently in a single reaction step and requires no expensive washing processes.

It has now been found in accordance with this invention, that silyl derivatives of purine and pyrimidine bases, and compounds derived therefrom, react readily and in good yields with blocked, preferably peracylated polysaccharides, in the presence of a Friedel-Crafts catalyst or of a trialkylsilyl ester, preferably a trimethylsilyl ester of a mineral acid or a strong organic acid to yield N-glycosyl derivatives.

SUMMARY OF THE INVENTION

The nucleosides of this invention are polysaccharidylamides characterized by at least ten monosaccharides units in the saccharidyl group and the amido group being a saturated or unsaturated monocyclic or fused bicyclic heterocyclic amido wherein the amido nitrogen atom attached to the saccharidyl group is a ring member of a 5-6 membered ring containing 1-3 nitrogen atoms as hetero atoms, including mono- and bicyclic compounds of the pyrrole, pyrazole, triazole, pyridine, diazine and triazine series.

In a compositional aspect, this invention relates to N-(polysaccharidyl)-nucleosides of Formula I

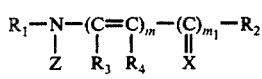

wherein

Z is a carbohydrate residue of at least 10 monosaccharide units, whose OH groups are free or blocked by alkanoyl, arylalkyl or aroyl of up to 10 carbon atoms;

X is O or S;

$m$ is 0 or 1;

$m_1$ is 0 or 1;

$R_1$ and $R_2$ collectively are saturated or unsaturated alkylene of 1–4 carbon atoms or a corresponding saturated or unsaturated alkylene wherein 1–2 carbon atoms in the chain are replaced by a nitrogen atom or a corresponding alkylene or aza-substituted alkylene substituted by 1 or 2 of lower alkyl, lower alkenyl, aryl, aralkyl, acyl or alkanoyl, alkoxy, acyloxy or alkanoyloxy, alkoxycarbonyl or dialkylaminocarbonyl of up to 10 carbon atoms, trifluoromethyl, hydroxy, oxo, carboxamido, amino, nitro, nitriloxo or halogen;

$R_3$ and $R_4$ each are hydrogen, alkyl of up to 6 carbon atoms, alkoxycarbonyl of up to 6 carbon atoms, alkylaminocarbonyl of up to 6 carbon atoms, carboxyl or nitrile or collectively are

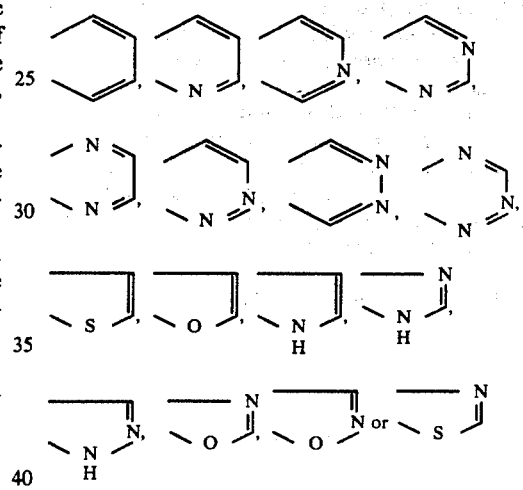

or a corresponding hydrogenated analog thereof or a corresponding analog thereof substituted by lower alkyl, lower alkenyl, aryl, aralkyl, acyl or alkanoyl, alkoxy, acyloxy or alkanoyloxy, alkoxycarbonyl or dialkylaminocarbonyl of up to 6 10carbon atoms, trifluoromethyl, hydroxy, oxo, carboxamido, amino, nitro, nitriloxo or halogen.

In another compositional aspect, this invention relates to partially novel silylnucleoside intermediates of Formula II

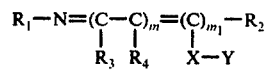

wherein $R_1$, $R_2$, $R_3$, $R_4$, X, $m$ and $m_1$ are as above and Y is alkylsilyl or trialkylsilyl of up to 4 carbon atoms per alkyl.

In another compositional aspect, this invention relates to novel silylnucleoside intermediates of Formula III

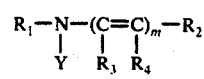

wherein $R_1$, $R_2$, $R_3$, $R_4$, $m$ and Y are as above.

In a preparative aspect, this invention relates to preparing compounds of Formula I by reacting a 1-O-acyl, 1-O—alkyl, or 1-halogen derivative of a blocked polysaccharide with a compound of Formula II or III wherein $R_1$, $R_2$, $R_3$, $R_4$, X, m and $m_1$ are as above and Y is alkyl or trialkylsilyl of up to 4 carbon atoms per alkyl, in the presence of a Friedel-Crafts catalyst or of a trialkylsilyl ester, and, optionally, splitting off blocking groups.

In a method of use aspect, this invention relates to a method of separating a mixture of nucleosides, nucleotides and polynucleotides as well as proteins having a particular affinity to the corresponding base comprising passing a solution of the mixture in a buffer over a compound of Formula I, whereby the compound selectively interacts with a component of said mixture and another component of said mixture is eluted with the buffer.

DETAILED DISCUSSION $R_1$ and $R_2$ are a bivalent radical, i.e., saturated or unsaturated lower alkylene, preferably of 1–4 carbon atoms, for example, methylene, ethylene, propylene, or tetramethylene residues which can optionally be interrupted by one or two hetero atoms, preferably nitrogen and/or oxygen.

Bivalent radicals $R_1$ and $R_2$, and $R_3$ and $R_4$ can be substituted by, for example, lower alkyl, lower alkenyl, aryl, aralkyl, trifluoromethyl, acyl or alkanoyl, hydroxy, alkoxy, acyloxy or alkanoyloxy, carboxyl, oxo, carboxamido, alkoxycarbonyl or dialkylaminocarbonyl of up to 10 carbon atoms, amino, nitro, nitriloxo, or halogen.

$R_1$ and $R_2$ preferably mean the following:

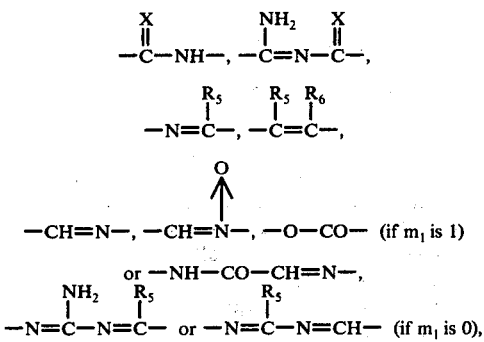

wherein X is as above and $R_5$ and $R_6$ are hydrogen, alkyl, alkoxycarbonyl, or alkylaminocarbonyl of up to 6 carbon atoms.

Silylated organic bases of Formulas II and III are starting materials in which $R_1$ and $R_2$ are linked in a ring, preferably so that the heterocyclic base contain five or six atoms, including one to three nitrogen atoms, in the ring.

Silylated organic bases of Formulas II and III are derived preferably from the following heterocyclic bases:

Uracil, cytosine, 6-azauracil, 2-thio-6-azauracil, thymine, adenine, guanine, lumazine, imidazole, pyrazine, thiazole, triazole, any of which can bear substituents as described above for $R_1$, $R_2$, as well as by $R_3$ and $R_4$.

Polysaccharides within the scope of the present invention means carbohydrates already possessing reducing end groups or wherein such groups are produced under the reaction conditions by cleavage of glycosidic linkages. Polysaccharides include, but are not limited to, sugars containing at least 10–12 monosaccharide units, for example, cellulose, amylose (starch), inulin, agarose, dextrins and polypentosans. Cellulose, amylose, and agarose are preferred. Preferably, free hydroxy groups of the sugars are blocked with alkanoyl, aralkyl or aroyl blocking groups of up to 10 carbon atoms customary in sugar chemistry, for example, acetyl, propionyl, benzoyl, p-chlorobenzoyl, p-toluyl, and benzyl.

Preferred compounds of this invention are those wherein the total number of ring members in the ring system described by

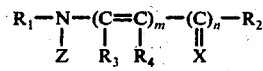

is 5 or 6.

Preferred compounds of this invention are compounds of Formula I wherein:

(a) Z is a carbohydrate residue, the OH of which are free;

(b) Z is a carbohydrate residue, the OH of which are blocked by alkanoyl, alkyl, aralkyl or aroyl of up to 10 carbon atoms;

(c) X is O, including (a)–(b);

(d) X is S, including (a)–(b);

(e) m is 0, including (a)–(d);

(f) m is 1, including (a)–(d);

(g) $m_1$ is 0, including (a)–(f);

(h) $m_1$ is 1, Including (a)–(f);

(i) $R_1$ and $R_2$ collectively are saturated or unsaturated alkylene of 1–4 carbon atoms, including (a)–(h);

(j) $R_1$ and $R_2$ collectively are saturated or unsaturated azaalkylene of up to 4 carbon and nitrogen atoms, including (a)–(h);

(k) $R_1$ and $R_2$ collectively are saturated or unsaturated diazaalkylene of up to 4 carbon and nitrogen atoms, including (a)–(h);

(l) $R_1$ and $R_2$ collectively are

including (a)–(h);

(m) $R_1$ and $R_2$ collectively are

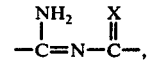

including (a)–(h);

(n) $R_1$ and $R_2$ collectively are

including (a)–(h);

(o) $R_1$ and $R_2$ collectively are

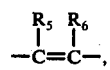

including (a)–(h);

(p) $m_1$ is 1 and $R_1$ and $R_2$ collectively are —CH=N—, including (a)–(f);

(q) $m_1$ is 1 and $R_1$ and $R_2$ collectively are

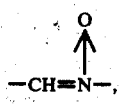

including (a)–(f);

(r) $m_1$ is 1 and $R_1$ and $R_2$ collectively are —NH—CO—CH=N—, including (a)–(f);

(s) $m_1$ is 0 and $R_1$ and $R_2$ collectively are

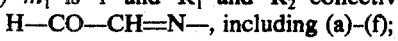

including (a)–(f);

(t) $m_1$ is 0 and $R_1$ and $R_2$ collectively are

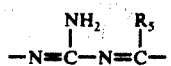

including (a)–(f);

(u) $R_3$ and $R_4$ independently are hydrogen, alkyl of up to 6 carbon atoms, alkoxycarbonyl of up to 6 carbon atoms, alkylaminocarbonyl of up to 6 carbon atoms, carboxyl or nitrile, including (a)–(t);

(v) $R_3$ and $R_4$ collectively are

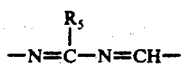

including (a)–(t);

(w) $R_3$ and $R_4$ collectively are

including (a)–(t);

(x) $R_3$ and $R_4$ collectively are

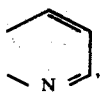

including (a)–(t);

(y) $R_3$ and $R_4$ collectively are

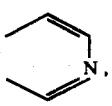

including (a)–(t);

(z) $R_3$ and $R_4$ collectively are

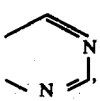

including (a)–(t);

(aa) $R_3$ and $R_4$ collectively are

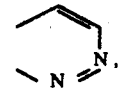

including (a)–(t);

(bb) $R_3$ and $R_4$ collectively are

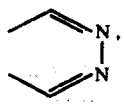

including (a)–(t);

(cc) $R_3$ and $R_4$ collectively are

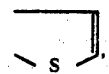

including (a)–(t);

(dd) $R_3$ and $R_4$ collectively are

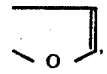

including (a)–(t);

(ee) $R_3$ and $R_4$ collectively are

including (a)–(t);

(ff) $R_3$ and $R_4$ collectively are

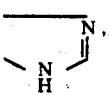

including (a)–(t);

(gg) $R_3$ and $R_4$ collectively are

including (a)–(t);

(hh) $R_3$ and $R_4$ collectively are

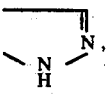

including (a)–(t);

(ii) $R_3$ and $R_4$ collectively are including (a)–(t);
(jj) $R_3$ and $R_4$ collectively are

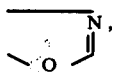

including (a)–(t);
(kk) $R_3$ and $R_4$ collectively are

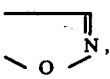

including (a)–(t);

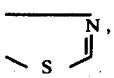

including (a)–(t);
(ll) Z is cellulose, including (a)–(kk);
(mm) Z is amylose, including (a)–(kk); and
(nn) Z is agarose, including (a)–(kk).

Specific examples of compounds of this invention are $N^1$-[(1→4)-β-glucopyranosyl]$_n$-cytosine wherein $n$ is from 11 to 100; $N^1$-[(1→4)-β-D-glucopyranosyl]$_n$-uracil wherein $n$ is from 11 to 100; $N^9$-[(1→4)-β-D-glucopyranosyl]$_n$-adenine wherein $n$ is from 11 to 100; $N^9$-[(1→4)-β-D-glucopyranosyl]$_n$6-(2-methyl-2-buten-4-yl)-adenine wherein $n$ is about 33; $N^1$-[(1→4)-α-D-glucopyranosyl]$_n$-cytosine wherein $n$ is about 38; and $N^1$-[galactopyranoxyl]$_n$-cytosine wherein $n$ is about 44.

This invention concerns a process in accordance with Patent Application P 1 919 307.8, incorporated herewith by reference (see U.S. 3,748,320), for the preparation of nucleosides of Formula I.

Friedel-Crafts catalysts include, generally, compounds disclosed at G.A. Ohlah Friedel-Crafts and related reactions, I general aspects, 1963, Interscience Publishers J. Wiley & Sons New York and London.

Friedel-Crafts catalysts preferred for the reaction are those soluble in the solvents used, e.g., $SnCl_4$, $TiCl_4$, $ZnCl_2$ and $BF_3$-etherate.

Trialkylsilyl esters used as catalysts are preferably derived from oxygen acids. Trimethylsilyl esters of mineral acids or strong organic acids are preferred. Particularly preferred are readily obtainable mono- or polytrimethylsilyl esters as reported, for example, by U. Wannagat and W. Liehr, "Angew. Chemie" (Applied Chemistry) 69, 783 (1957); and H. C. Marsmann and H. G. Horn, "Z. Naturforschung" (Journal of Natural Sciences) B 27, 4448 (1972). Trimethylsilyl is particularly preferred.

Of trialkylsilyl esters derived from mineral acids, those from $H_2SO_4$ or $HClO_4$ are preferred. A preferred catalyst is trimethylsilyl perchlorate. Of the trialkylsilyl esters are derived from organic acids, trifluoromethanesulfonate is especially preferred.

Exemplary of solvents for the reaction are methylene chloride, ethylene chloride, chloroform, dioxane, tetrahydrofuran, acetonitrile, dimethylformamide, benzene, toluene, carbon disulfide, chlorobenzene, nitromethane or mixtures thereof.

The reaction can be conducted at room temperature or at higher or lower temperatures, preferably in the range 0°–160° C.

Reactants are employed in approximately equimolar quantities. If non-reducing sugars are utilized, the amount of the catalyst must be increased proportionately, since a portion of the catalyst is required to cleave glycosidic linkages to form reducing end groups.

If a compound of Formula II or III and catalyst is utilized in excess, based on polysaccharide, the number of monosaccharide units in the polysaccharide linked to the nitrogen compound is decreased by cleavage. In other words, alteration of the reaction conditions can affect the size of the polysaccharide residue introduced in the product of Formula I.

If compounds required for the reaction in accordance with Formulas II or III contain groups which are attacked by the catalyst under conditions effecting cleavage of glycosidic linkages, cleavage of the polysaccharide to obtain smaller units and/or to form reducing end groups can be carried out in a preceding step so that, during the cleavage, suitably reactive 1-O-acyl, 1-O-alkyl, or 1-halogen compounds of blocked polysaccharide are produced. The reaction of this invention can then be conducted, for example, with 1-halogen compounds, in the presence of minimal amounts of catalyst and under extremely mild conditions (0° C.). In the foregoing, 1-O-acyl includes alkanoyl of up to 6 carbon atoms and 1-O-alkyl includes alkyl of up to 6 carbon atoms.

Compounds of Formula I with free hydroxy groups can be prepared by removing blocking groups in a known manner, for example, by alcoholic solutions of ammonia or alcoholates, by aqueous or alcoholic alkali or, in the case of benzyl ethers, by reduction or hydrogenation.

The free or blocked polysaccharide residue in the nucleosides of this invention is linked to the nitrogen atom preferably in the form of a β-glycoside.

The products obtained are freed of soluble, low-molecular products by treatment with water and ethanol; this step can be accomplished in conjunction with removing the blocking groups.

The heterocyclic products linked to polysaccharides have surprisingly good properties as sorbents for the separation of nucleoside and nucleotide mixtures, especially with respect to separating power and time required.

Moreover, they possess valuable biological properties, for example, an effect stimulating the immune system.

The polymers containing uracil or thymine are very well suited for the selective separation of m-RNA containing poly-A sequences whereas ribosomal RNA is not retained.

Furthermore, polymers containing $N^7$-methylated guanine can be used to induce antibodies to $N^7$-methylguanosine and its nucleotides.

Examples of preferred products of the invention are:

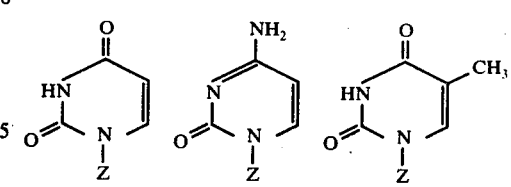

-continued

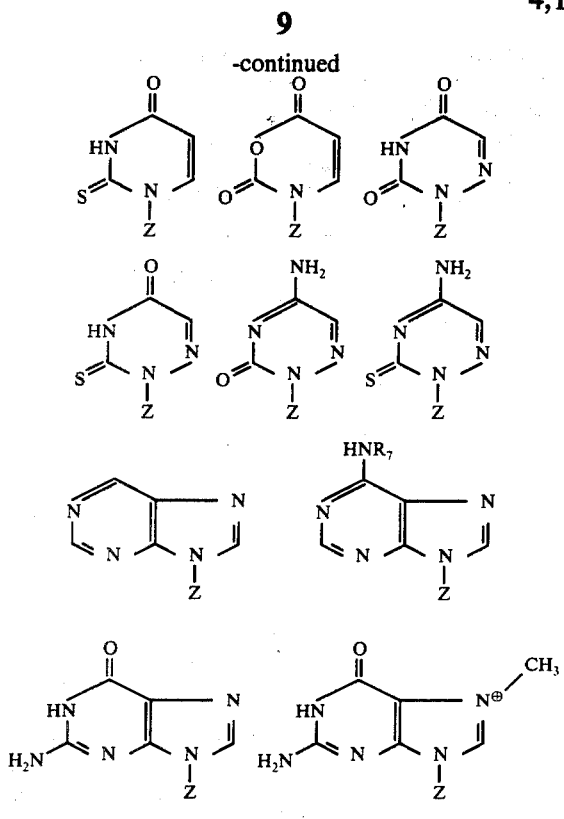

wherein Z is as in Formula I.

R₇ can be hydrogen, lower alkyl, lower alkenyl, aryl, or aralkyl. Lower alkyl is preferably of 1–6 carbon atoms, lower alkenyl of 3–6 carbon atoms, for example, 2-methyl-2-buten-4-yl. Aryl can have up to 10 carbon atoms and aralkyl up to 10 carbon atoms.

The content of monosaccharides in any particular molecule results from statistical distribution. The average number of monosaccharide units of the polysaccharide linked by an N-glycoside bond to the heterocyclic ring system can be determined from nitrogen content according to combustion analysis.

Results for cytosine, linked to a polysaccharide containing 25 glucose units are:

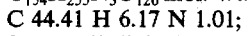
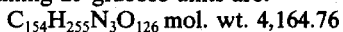

for uracil, linked to a polysaccharide containing 70 glucose units:

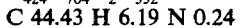

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A suspension was prepared from 500 ml. of absolute 1,2-dichloroethane and 10 g. of triacetylcellulose. After the addition of 15 millimoles of 2,4-O,N-bis(trimethylsilyl)-4-amino-2-hydroxypyrimidine in 20 ml. of absolute acetonitrile and a solution of 8 g. (60 millimoles) of AlCl₃ in 200 ml. of absolute acetonitrile, the mixture was refluxed overnight. After cooling, the mixture was diluted with 2 liters of methylene chloride and washed with saturated NaHCO₃ solution. The organic solution was filtered over kieselguhr which was rinsed with methylene chloride. The combined organic phases were dried (Na₂SO₄) and concentrated to dryness under vacuum. The residue was freed of traces of 1,2-dichloroethane by codistillation with methanol and was then suspended in 250 ml. of CH₃OH/NH₃ and stirred overnight at 0° C. A fluffy powder was thus formed which was vacuum-filtered over a porous plate and washed with hot methanol, moist methanol, and water. After drying under vacuum at 50° C., 4.27 g. of a yellowish powder was obtained.

Nitrogen content: 0.59%, corresponding to an average number of 44 monosaccharides.

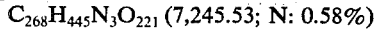

EXAMPLE 2

A suspension of 5 g. of triacetylcellulose in 400 ml. of 1,2-dichloroethane was combined with 300 mmol of O,N-bis (trimethylsilyl) -4-amino-2-hydroxypyrimidine as well as 10 ml. (85.5 mmol) of SnCl₄ in 100 ml. of 1,2-dichloroethane. The mixture was heated to boiling, thus dissolving a portion of the triacetylcellulose. A complete dissolution was reached only after the addition of 30 ml. of acetonitrile. After 3 hours of refluxing, another 30 mmol of silyl compound and another 4 ml. (34.2 mmol) of SnCl₄ were added to the mixture. The procedure was repeated. The reaction was terminated after a total time of 24 hours. The reaction mixture was worked up as set forth in Example 1. After methanolysis, washing, and drying, 1.6 g. of a powder remained.

Nitrogen content: 0.71%, corresponding to an average number of 36 monosaccharides.

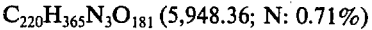

EXAMPLE 3

(a) Acetylating Cleavage of the Triacetylcellulose:

40 g. of triacetylcellulose was dissolved in a mixture of 400 ml. of acetic acid and 200 ml. of acetic anhydride. After the addition of 20 ml. of concentrated H₂SO₄ in 50 ml. of acetic anhydride, the mixture was agitated for one day at room temperature and then poured into 5 liters of ice water and brought to pH 4–5 with Na₂CO₃. The sediment was vacuum-filtered after allowing the mixture to stand overnight, washed with water, and extracted twice with hot methanol. The insoluble portion was dried under vacuum at 50° C.

Yield: 36.7 g.

(b) Reaction to the Cytosine Derivative:

6 g. of the product obtained according to 3(a) was dissolved at 60° C. in 500 ml. of 1,2-dichloroethane. After adding 20 mmol of O,N-bis(trimethylsilyl)-4-amino-2-hydroxypyrimidine in 40 ml. of acetonitrile, as well as 4.2 ml. (35.9 mmol) of SnCl₄ in 40 ml. of 1,2-dichloroethane, the mixture was refluxed for 2 hours. A clear, yellow solution was thus obtained which was worked up as described in Example 1. After methanolysis, washing, and drying, 2.5 g. of a fluffy powder remained.

Nitrogen content: 0.73%, corresponding to an average number of 35 monosaccharides.

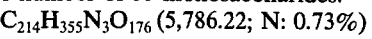

EXAMPLE 4

6 g. of the product obtained in accordance with 3(a) was dissolved at 60° C. in 500 ml. of 1,2-dichloroethane.

11

After the addition of 24 mmol of 2,4-bis(trimethylsilyloxy)pyrimidine and 4.2 ml. (35.9 mmol) of SnCl$_4$ in 100 ml. of 1,2-dichloroethane, the mixture was refluxed for 2 hours. After cooling, the reaction mixture was worked up as set forth in Example 1.

After methanolysis, washing, and drying, there remained 2.02 g. of a fluffy powder.

Nitrogen content: 0.47%, corresponding to an average number of 36 monosaccharides.

$C_{220}H_{364}N_2O_{182}$ (5,949.35; N: 0.47%)

EXAMPLE 5

6 g. of the product obtained according to 3(a) was dissolved at 60° C. in 500 ml. of 1,2-dichloroethane. After adding 20 mmol of 6-(benzoyl)-trimethylsilylamino-9-trimethylsilylpurine and 4.2 ml. (35.9 mmol) of SnCl$_4$ in 100 ml. of 1,2-dichloroethane, the reaction mixture was refluxed for 2.5 hours. After cooling, the mixture was worked up as described in Example 1.

The residue was suspended in 150 ml. of methanol, combined with 50 ml. of 1N NaOCH$_3$ solution, and refluxed for 2 hours. The cooled solution was neutralized with acetic acid and vacuum-filtered over a porous plate. Washing and drying yielded 3.4 g. of a powder.

Nitrogen content: 1.31%, corresponding to an average number of 32 monosaccharides.

$C_{197}H_{325}N_5O_{160}$ (5,323.81; N: 1.32%)

EXAMPLE 6

Reaction to the Cytosine Derivative:

6 g. of the product obtained according to 3(a) was dissolved at 60° C. in 500 ml. of 1,2-dichloroethane. After the addition of 20 mmol of O,N-bis(trimethylsilyl)-4-amino-2-hydroxypyrimidine in 40 ml. of acetonitrile, the mixture was combined with 25 mmol of trimethylsilyl perchlorate in 80 ml. of benzene, and the solution was refluxed for 3 hours. The solvent was then removed under vacuum. The residue was suspended in 250 ml. of NH$_3$/CH$_3$OH and agitated overnight, yielding a fluffy powder which was vacuum-filtered and washed with methanol, moist methanol, and water. After drying under vacuum at 50° C., 3.16 g. of the final product was obtained.

Nitrogen content: 0.69%, corresponding to an average number of 37 monosaccharides.

$C_{226}H_{375}N_3O_{186}$ (6,110.51; N: 0.69%)

EXAMPLE 7

(a) Acetylating Cleavage of the Triacetylcellulose:

30 g. of triacetylcellulose was dissolved under heating in 400 ml. of glacial acetic acid and combined, after cooling, with a solution of 30 ml. of concentrated H$_2$SO$_4$ in 300 ml. of acetic anhydride while cooling with ice water. The solution was agitated for 60 hours at room temperature and then poured into 5 l. of ice water and brought to pH 4–5 with Na$_2$CO$_3$. The precipitate was vacuum-filtered, after allowing the mixture to stand overnight, and then washed with hot water and extracted three times with hot methanol. The insoluble portion was dried under vacuum at 50° C. Yield: 25.2 g.

(b) Reaction to the Cytosine Derivative:

6 g. of the product obtained as set forth in (a) was dissolved in 500 ml. of 1,2-dichloroethane at 60° C. After adding 20 mmol of O,N-bis(trimethylsilyl)-4-amino-2-hydroxypyrimidine in 40 ml. of acetonitrile as well as 6.5 ml. (55.6 mmol) of SnCl$_4$ in 100 ml. of 1,2-dichloroethane, the mixture was refluxed for 2 hours,

12 yielding a clear solution which was worked up as described in Example 1. After methanolysis, washing, and drying, 3.32 g. of a fluffy powder remained.

Nitrogen content: 0.91%, corresponding to an average number of 28 monosaccharides.

$C_{172}H_{285}N_3O_{141}$ (4,651.20; N: 0.90%)

EXAMPLE 8

6 g. of the product obtained in accordance with 3(a) was dissolved at 60° C. in 500 ml. of 1,2-dichloroethane. After adding 24 mmol of 6-(2-methyl-but-2-en-4-yl)-trimethylsilylamino9-trimethylsilylpurine and 4.2 ml. (35.9 mmol) of SnCl$_4$ in 100 ml. of 1,2-dichloroethane, the mixture was refluxed for 2.5 hours. After cooling, the mixture was worked up as described in Example 1. Methanolysis, washing, and drying yielded 3.3 g. of a fluffy powder.

Nitrogen content: 1.26%, corresponding to an average number of 33 monosaccharides.

$C_{208}H_{343}N_5O_{165}$ (5,554.07; N: 1.26%)

EXAMPLE 9

6 g. of amylose triacetate (prepared according to J. E. Hodge, Methods in Carbohydrate Chemistry, vol. IV, Academic Press, New York and London, 1964) was dissolved in 500 ml. of 1,2-dichloroethane. After adding 20 mmol of O,N-bis(trimethylsilyl)-4-amino-2-hydroxypyrimidine in 40 ml. of acetonitrile as well as 6.5 ml. (55.6 mmol) of SnCl$_4$ in 100 ml. of 1,2-dichloroethane, the mixture was refluxed for 2 hours. After cooling, the mixture was worked up analogously to Example 1. The blocking groups on the sugar were removed by methanolysis with CH$_3$OH/NH$_3$. The methanol-insoluble residue was vacuum-filtered, washed with methanol, and dried. Yield: 2.8 g.

Nitrogen content: 0.67%, corresponding to an average number of 38 monosaccharides.

$C_{232}H_{385}N_3O_{191}$ (6,272.66; N: 0.67%)

EXAMPLE 10

6 g. of acetylated agarose (prepared according to J. N. BeMiller, Methods in Carbohydrate Chemistry, vol. V, Academic Press, New York and London, 1965) was dissolved in 500 ml. of 1,2-dichloroethane. After the addition of 20 mmol of O,N-bis(trimethylsilyl)-4-amino-2-hydroxypyrimidine in 40 ml. of acetonitrile as well as 6.5 ml. (55.6 mmol) of SnCl$_4$ in 100 ml. of 1,2-dichloroethane, the mixture was refluxed for 2 hours. After cooling, the mixture was worked up as described in Example 1. The blocking groups on the sugar were removed by methanolysis with CH$_3$OH/NH$_3$. The methanol-insoluble residue was vacuum-filtered, washed with methanol, and dried. Yield: 2.6 g.

Nitrogen content: 0.59%, corresponding to an average number of 44 monosaccharides.

$C_{268}H_{401}N_3O_{199}$ (6,849.18; N: 0.61%)

EXAMPLE 11

A suspension of 2.5 g. of triacetylcellulose in 150 ml. of 1,2-dichloroethane was combined with 6 mmol of O,N-bis(trimethylsilyl)-4-amino-2-hydroxypyrimidine and 2 g. (15 mmol) of AlCl$_3$, dissolved in 50 ml. of acetonitrile. The mixture was refluxed, thus producing a solution. After refluxing overnight, the mixture was worked up as disclosed in Example 1. After methanolysis, washing, and drying, there remained 1.27 g. of a fluffy powder.

Nitrogen content: 0.26%, corresponding to an average number of 101 monosaccharides.

$C_{610}H_{1015}N_3O_{506}$ (16,487.85; N: 0.26%)

EXAMPLE 12

A suspension of 6 g. of triacetylcellulose in 500 ml. of 1,2-dichloroethane was combined with 20 mmol of 2,4-bis(trimethylsilyloxy)pyrimidine and 4.2 ml. of SnCl$_4$ in 100 ml. of acetonitrile. The mixture was refluxed, thus producing a solution. After refluxing overnight, the mixture was worked up as set forth in Example 1. Methanolysis, washing, and drying yielded 3.13 g. of a fluffy powder.

Nitrogen content: 0.17%, corresponding to an average number of 99 monosaccharides.

$C_{598}H_{994}N_2O_{497}$ (16,164.55; N: 0.17%)

EXAMPLE 13

A suspension of 6 g. of triacetylcellulose in 500 ml. of 1,2-dichloroethane was combined with 20 mmol of 6-(octanoyl)trimethylsilylamino-9-trimethylsilylpurine and 4.2 ml. (35.9 mmol) of SnCl$_4$ in 100 ml. of acetonitrile. The mixture was refluxed, thus producing a solution. The mixture was then refluxed overnight and worked up analogously to Example 1.

The residue was suspended in 150 ml. of methanol, combined with 50 ml. of 1N NaOCH$_3$ solution, and refluxed for 2 hours. The cooled solution was neutralized with acetic alcid and vacuum-filtered over a porous plate. After washing and drying, 3.2 g. of a powder remained.

Nitrogen content: 0.44%, corresponding to an average number of 98 monosaccharides.

$C_{593}H_{985}N_5O_{490}$ (16,025.44; N: 0.44%)

EXAMPLE 14

A solution of 6 g. of the product obtained in accordance with Example 7(a) in 500 ml. of 1,2-dichloroethane was combined with 20 mmol of 2,6,9-O,N-tris(-trimethylsilyl)-2-acetamido-6-hydroxypurine as well as 6.5 ml. (55.6 mmol) of SnCl$_4$ in 100 ml. of 1,2-dichloroethane. The mixture was then refluxed for 2 hours and worked up as described in Example 1.

The residue was suspended in 150 ml. of methanol, mixed with 50 ml. of 1N NaOCH$_3$ solution, and refluxed for 2 hours. The cooled solution was neutralized with acetic acid and vacuum-filtered over a porous plate. Washing and drying yielded 3.1 g. of a powder.

Nitrogen content: 1.34%, corresponding to an average number of 31 monosaccharides.

$C_{191}H_{315}N_5O_{156}$ (5,177.66; N: 1.35%)

EXAMPLE 15

A suspension of 6 g. of triacetylcellulose in 500 ml. of 1,2-dichloroethane was combined with 20 mmol of 2,6,9-tris(trimethylsilyl)-2-acetamido-6-hydroxypurine as well as 6.5 ml. (55.6 mmol) of SnCl$_4$ in 100 ml. of 1,2-dichloroethane. The mixture was then refluxed for 2 hours and worked up in accordance with Example 1.

The residue was suspended in 150 ml. of methanol, combined with 50 ml. of 1N NaOCH$_3$ solution, and refluxed for 2 hours. The cooled solution was neutralized with acetic acid and vacuum-filtered over a porous plate. After washing and drying, 3.0 g. of a powder remained.

Nitrogen content: 0.43%, corresponding to an average number of 98 monosaccharides.

$C_{593}H_{985}N_5O_{491}$ (16,041.44; N: 0.44%)

EXAMPLE 16

Acetylating Cleavage of Triacetylcellulose:

Under agitation and cooling with tap water, respectively 330 ml. of an ice-cold mixture of 300 ml. of acetic anhydride and 30 ml. of concentrated H$_2$SO$_4$ was added to respectively 30 g. of triacetylcellulose in 300 ml. of acetic acid. After the predetermined time period had elapsed, the reaction was terminated by pouring the mixture into 5 l. of ice water. By adding Na$_2$CO$_3$, a pH of 4–5 was set in the mixture. The latter was allowed to stand overnight, and then the precipitate was vacuum-filtered, washed with water, and extracted with cold methanol.

The methanol-insoluble proportion was dried under vacuum at 50° C.

(a) This batch was worked up after 71 hours; yield: 18.5 g.

(b) This batch was worked up after 76 hours; yield: 14.8 g.

(c) This batch was worked up after 84 hours; yield: 9.5 g.

EXAMPLE 17

6 g. of the product obtained in accordance with Example 16(c) was dissolved in 500 ml. of 1,2-dichloroethane. After the addition of 20 mmol of O,N-bis(trimethylsilyl)-4-amino-2-hydroxypyrimidine in 40 ml. of acetonitrile as well as 4.2 ml. (35.9 mmol) of SnCl$_4$ in 100 ml. of 1,2-dichloroethane, the mixture was refluxed for 2 hours. After cooling, the mixture was worked up as set forth in Example 1. Methanolysis, washing, and drying yielded 3.2 g. of a fluffy powder.

Nitrogen content: 2.22%, corresponding to an average number of 11 monosaccharides.

$C_{70}H_{115}N_3O_{56}$ (1,894.71; N: 2.22%)

EXAMPLE 18

6 g. of the product obtained according to Example 16(c) was dissolved in 500 ml. of 1,2-dichloroethane. After the addition of 24 mmol of 2,4-bis(trimethylsilyloxy)pyrimidine and 4.2 ml. (35.9 mmol) of SnCl$_4$ in 100 ml. of 1,2-dichloroethane, the mixture was refluxed for 2 hours. After cooling, the mixture was worked up as described in Example 1. Methanolysis, washing, and drying yielded 3.1 g. of a powder.

Nitrogen content: 1.47%, corresponding to an average number of 11 monosaccharides.

$C_{70}H_{114}N_2O_{57}$ (1,895.70; N: 1.48%)

EXAMPLE 19

6 g. of the product as obtained in Example 16(c) was dissolved in 500 ml. of 1,2-dichloroethane. After adding 20 mmol of 6-(octanoyl)-trimethylsilylamino-9-trimethylsilylpurine and 4.2 ml. (35.9 mmol) of SnCl$_4$ in 100 ml. of 1,2-dichloroethane, the reaction mixture was refluxed for 2 hours. After cooling, the mixture was worked up analogously to Example 1. The residue was suspended in 150 ml. of methanol, combined with 50 ml. of 1N NaOCH$_3$ solution, and refluxed for 2 hours. The cooled solution was neutralized with acetic acid and vacuum-filtered over a porous plate. There remained 3.1 g. of a powder after washing and drying.

Nitrogen content: 3.65%, corresponding to an average number of 11 monosaccharides.

$C_{71}H_{115}N_5O_{55}$ (1,918.74; N: 3.65%)

EXAMPLE 20

6 g. of the product prepared according to Example 16(c) was dissolved in 500 ml. of 1,2-dichloroethane. After the addition of 20 mmol of 2,6,9-tris(trimethylsilyl)-2-acetamido-6-hydroxypurine as well as 6.5 ml. (55.6 mmol) of $SnCl_4$ in 100 ml. of 1,2-dichloroethane, the mixture was refluxed for 2 hours. After cooling, the reaction mixture was worked up as set forth in Example 1. The residue was suspended in 150 ml. of methanol, combined with 50 ml. of 1N $NaOCH_3$ solution, and refluxed for 2 hours. The cooled solution was neutralized with acetic acid and vacuum-filtered over a porous plate. Washing and drying yielded 2.9 g. of a powder.

Nitrogen content: 3.61%, corresponding to an average number of 11 monosaccharides.

$C_{71}H_{115}N_5O_{56}$ (1,934.74; N: 3.62%)

EXAMPLE 21

Separation of a Mixture of Cytidine and Guanosine

A mixture of cytidine (5 μmol) and guanosine (1 μmol) in 0.001N tris buffer, pH = 7.5, was introduced to a column (1 × 2.5 cm.) of 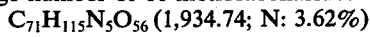-β-D-glucopyranosyl]-4-amino-1,2-dihydropyrimidin-2-one (nitrogen content 0.73%). The cytidine was eluted with the buffer, whereas the guanosine was recovered quantitatively. The guanosine could be eluted with the buffer 0.1N on NaCl.

EXAMPLE 22

To 36 g peracetylated cellulose (obtained by 50-60 hours acetylating cleavage according to example 16) in 500 ml absolute 1,2-dichloroethane, 90 ml of a solution of 2,4-bis-trimethyl silyloxy pyrimidine (60 mmol) in 1,2-dichloroethane and subsequently 134.5 ml of a solution of $(CH_3)_3SiSO_3CF_3$ (60 mmol, prepared according to Marsmann and Horn, Z. Naturforschung, 27B 4448 (1972)) in 1,2-dichloroethane was added and the reaction mixture refluxed for 4 hours. After addition of further 60 mmol 2,4-trimethylsilyloxy-pyrimidin and 60 mmol $(CH_3)_3SiSO_3CF_3$ in 1,2-dichloroethane the reaction mixture was heated for further 50 hours. After cooling and dilution with 500 ml $CH_2Cl_2$ the mixture was added to 2 liters of $CH_2Cl_2$ and shaken with 2 liters of saturated $NaHCO_3$ solutions. After separation, the aqueous phase was reextracted with 2 × 500 ml $CH_2Cl_2$ and the combined extracts evaporated. The residue was suspended in 1 liter of acetone, filtered and the insoluble residue washed with 1 liter of acetone. The combined acetone solution was concentrated to 250 ml and 500 ml $CH_3OH$ added. The precipitate was again dissolved in acetone and the procedure repeated twice. The remaining insoluble material was saponified with 500 ml methanolic ammonia for 3-4 days at 24° C and the precipitate washed with methanol and ether. Finally the residue was extracted with 3 × 250 ml portions $H_2O$ on the steam bath, and the insoluble part washed with ethanol ether to yield after pulverizing and drying 11.1 g with 0,96% nitrogen, i.e., the product had an average chain length of 17 glucose units.

EXAMPLE 23

Glucose$_{20}$-U was equilibrated with a solution containing 10 mmol Tris-buffer (p$_H$ = 7,2) and 0.1 m NaCl and filled into a column. Then a solution of poly-A-$^{14}$-C in 10 mm Tris-buffer was filtered through a column. The poly A-$^{14}$C was completely retained on the column and only eluted with $H_2O$.

In contrast poly U-$^{14}$C was not retained on the column.

The preceding examples can be repeated with similar success by substituting the generically and specifically described reactants and/or operating conditions of this invention for those used in the preceding examples.

The mechanical stability and thus the flow rate of the resulting columns can be improved by admixture with suitable other material like ulite and cellulose powder. Furthermore, crosslinking of the polymers by typical bivalent agents like acid chlorides or dicarboxylic acids, e.g. oxalic acid, succinic acid, adipic acid, terephtalic acid or bis-isocyanates, bis-imino ether salts will improve and modify the mechanic stability and flow rate.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An N-(polysaccharidyl)-nucleoside of the formula

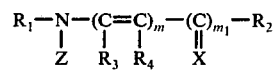

wherein Z is a polysaccharide moiety of a carbohydrate of at least 10 monosaccharide units and linked by a glycoside bond to the nitrogen atom, whose OH groups are free or blocked by alkanoyl, carbocyclic arylalkyl or carbocyclic aroyl, each of up to 10 carbon atoms;

X is O or S;

m is 0 or 1;

$m_1$ is 0 or 1;

$R_1$ and $R_2$ collectively are saturated or unsaturated alkylene of 1-4 carbon atoms or a corresponding saturated or unsaturated alkylene wherein 1-2 carbon atoms in the chain are replaced by a nitrogen atom or a corresponding alkylene or aza-substituted alkylene substituted by 1 or 2 of lower alkyl, lower alkenyl carbocyclic aryl, carbocyclic aralkyl, carbocyclic aroyl or alkanoyl, alkoxy, carbocyclic acyloxy or alkanoyloxy, alkoxycarbonyl or dialkylaminocarbonyl, each of up to 10 carbon atoms, trifluoromethyl, hydroxy, oxo, carboxamido, amino, nitro, nitriloxo or halogen;

$R_3$ and $R_4$ each are hydrogen, alkyl of up to 6 carbon atoms, alkoxycarbonyl of up to 6 carbon atoms, alkylaminocarbonyl of up to 6 carbon atoms, carboxyl or nitrile or collectively are

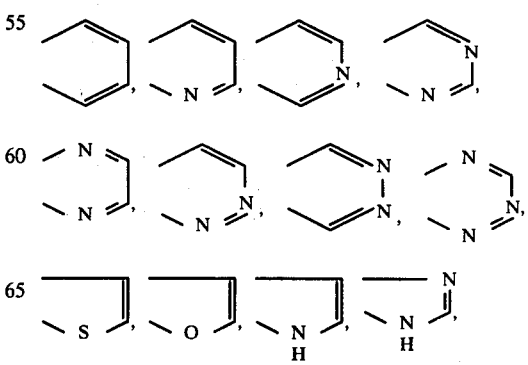

-continued

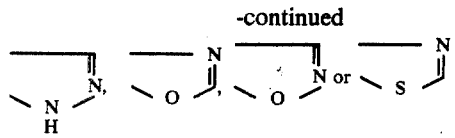

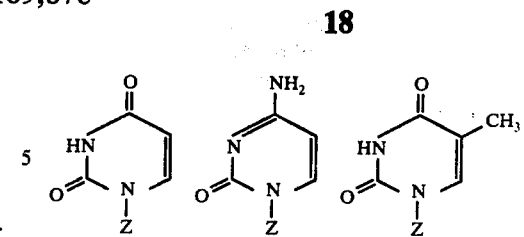

or a corresponding saturated divalent group or a corresponding divalent group substituted by lower alkyl, lower alkenyl, carbocyclic aryl carbocyclic aralkyl, carbocyclic aroyl, alkanoyl, alkoxy, carbocyclic aroyloxy, alkanoyloxy, alkoxycarbonyl or dialkylaminocarbonyl, each of up to 10 carbon atoms, trifluoromethyl, hydroxy, oxo, carboxamido, amino, nitro, nitriloxo or halogen.

2. $N^1$-[(1→4)-β-D-Glucopyranosyl]$_n$-cytosine wherein $n$ is from 11 to 100, a compound of claim 1.

3. $N^1$-[(1→4)-β-D-Glucopyranosyl]$_n$-uracil wherein $n$ is from 11 to 100, a compound of claim 1.

4. $N^9$-[(1→4)-β-D-Glucopyranosyl]$_n$-adenine wherein $n$ is from 11 to 100, a compound of claim 1.

5. $N^9$-[(1→4)-β-D-Glucopyranosyl]$_n$-6-(2-methyl-2-buten-4-yl)-adenine wherein $n$ is about 33, a compound of claim 1.

6. $N^1$-[(1→4)-α-D-Glucopyranosyl]$_n$-cytosine wherein $n$ is about 38, a compound of claim 1.

7. $N^1$-[Galactopyranosyl]$_n$-cytosine wherein $n$ is about 44, a compound of claim 1.

8. A compound of claim 1, wherein $m$ is 1.

9. A compound of claim 1, wherein $m$ is 1, $m_1$ is 1 and $R_1$ and $R_2$ collectively are —CH=N—.

10. A compound of claim 1, wherein $m$ is 0, $m_1$ is 0 and $R_1$ and $R_2$ collectively are

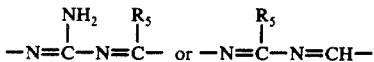

and $R_5$ is hydrogen, alkyl, alkoxycarbonyl or alkylaminocarbonyl, each of up to 6 carbon atoms.

11. A method of separating a mixture of buffer soluble nucleosides comprising passing a solution of the mixture of nucleosides in a buffer through a column formed of a compound of claim 1, whereby a nucleoside of said mixture is retained on the column and another nucleoside of said mixture is eluted therefrom the buffer.

12. An N-(polysaccharidyl)-nucleoside of claim 1 of the formula

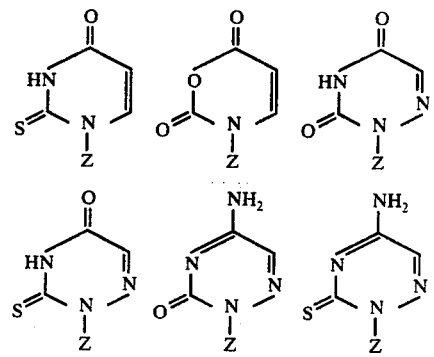

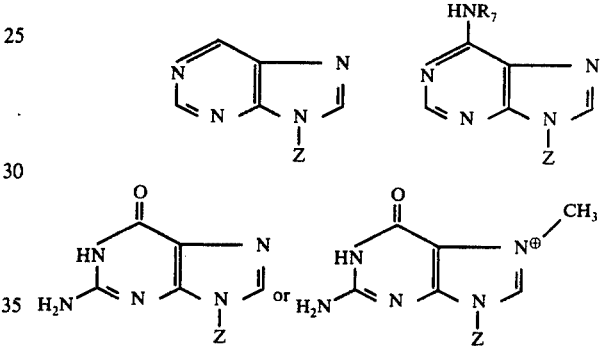

wherein Z is a polysaccharide moiety as defined therein and $R_7$ is hydrogen, alkyl of 1–6 carbon atoms, alkenyl of 3–6 carbon atoms, carbocyclic aryl of up to 10 carbon atoms or carbocyclic aralkyl of up to 10 carbon atoms.

13. An N-(polysaccharidyl)-nucleoside of claim 12 wherein Z is a cellulose, amylose, inulin, agarose, dextrin or polypentosan moiety.

14. An N-(polysaccharidyl)-nucleoside of claim 12 wherein Z is a cellulose, amylose or agarose moiety.

15. An N-(polysaccharidyl)-nucleoside of claim 12 wherein Z is a cellulose moiety.

* * * * *

UNITED STATES PATENT AND TRADEMARK OFFICE
CERTIFICATE OF CORRECTION

PATENT NO. : 4,109,078
DATED : August 22, 1978
INVENTOR(S) : HELMUT VORBRUGGEN ET AL It is certified that error appears in the above-identified patent and that said Letters Patent are hereby corrected as shown below:

Claim 1, line 44: reads "lower alkenyl carbocyclic:
should read -- lower alkenyl, carbocyclic --

Claim 1, second page, line 10: reads "carbocylcic aryl carboncyclic:
should read -- carbocyclic aryl, carbocyclic --

Claim 11, line 47: reads "therefrom the buffer"
should read -- therefrom with the buffer --

Signed and Sealed this

Twenty-seventh Day of March 1979

[SEAL]

Attest:

RUTH C. MASON
Attesting Officer

DONALD W. BANNER
Commissioner of Patents and Trademarks